US005113897A

United States Patent [19]

Kummerfeld et al.

[11] Patent Number: 5,113,897

[45] Date of Patent: May 19, 1992

[54] HEIGHT-ADJUSTABLE SUPPLY UNIT FOR RECEIVING WORKING DEVICES, ESPECIALLY MEDICAL DEVICES

[75] Inventors: Ryszard Kummerfeld, Lübeck-Travemünde; Siegfried Baumgarten; Gerd Holzapfel, both of Lübeck; Wolfgang Falb, Krummesse; Ulrich Palm, Norderstedt, all of Fed. Rep. of Germany

[73] Assignee: Drägerwerk Aktiengesellschaft, Lübeck, Fed. Rep. of Germany

[21] Appl. No.: 721,965

[22] Filed: Jun. 27, 1991

[30] Foreign Application Priority Data

Jul. 2, 1990 [DE] Fed. Rep. of Germany ....... 4021013

[51] Int. Cl.[5] ........................ F16L 5/00; B42F 13/00; A61M 5/00

[52] U.S. Cl. .............................. 137/357; 137/355.17; 248/129; 248/343; 604/259

[58] Field of Search ............... 137/343, 356, 357, 597, 137/355.16, 355.17, 560; 604/259; 248/129, 343

[56] References Cited

U.S. PATENT DOCUMENTS

| | | | |
|---|---|---|---|
| 2,345,224 | 3/1944 | Upp | 137/343 |
| 3,431,937 | 3/1969 | Hettlinger et al. | 137/355.16 |
| 3,517,695 | 6/1970 | Eveleigh et al. | 137/355.17 |
| 3,653,401 | 4/1972 | Beeler et al. | 137/355.17 |
| 4,559,036 | 12/1985 | Wunsch | 604/259 |
| 4,657,004 | 4/1987 | Coffey | 604/259 |
| 4,944,292 | 7/1990 | Gaek et al. | 137/343 |
| 5,009,384 | 4/1991 | Gerke et al. | 248/343 |
| 5,038,819 | 8/1991 | Sutphen | 137/355.17 |

*Primary Examiner*—A. Michael Chambers

*Attorney, Agent, or Firm*—McGlew & Tuttle

[57] ABSTRACT

A medical supply unit with a height-adjustable connection head, e.g., in the form of a ceiling-mounted supply unit or ceiling lamp, is able to receive a working device, e.g., an anesthesiological apparatus, while ensuring reliable coupling for this purpose, so that the user will be able to perform a procedure reliably, with the working device being correctly connected. This is made possible by a coupling part 34 equipped with guide faces 35, with which a receiving part 14 engages, which is provided with complementarily extending receiving jaws 15 and which actuates—in the case of correctly fitting engagement—electrical contacts 18, such that the control elements 10 provided on a control panel 9 for height adjustment of the connection head 1 and/or for supplying the working device 30 with the media needed for operation are released.

20 Claims, 2 Drawing Sheets

HEIGHT-ADJUSTABLE SUPPLY UNIT FOR RECEIVING WORKING DEVICES, ESPECIALLY MEDICAL DEVICES

FIELD OF THE INVENTION

The present invention pertains to a medical supply unit with a height-adjustable connection head, to which a working device is supplied with media (gas, electricity) necessary for its operation. The media is supplied from supply ducts provided in the connection head coupled by a coupling part located on the working device and engaging in a receiving part located on the connection head.

BACKGROUND OF THE INVENTION

Such supply units are used mainly for medical purposes, where a height-adjustable and pivotable supply column with a connection head and is usually suspended from the ceiling of a room, on which a working device used in medical technology can be suspended. Such supply units are used especially when the working device is to be moved into different positions in terms of height and pivoting movement in the room in question.

Whether or not the floor path is free does not need to be taken into account when changing places. The supply unit has with it all the supply connections which remain coupled to the working device during the entire movement. Thus, the user is able to conveniently move the needed working devices into the desired working position and to the corresponding site of work. Both the height adjustment and the area-covering pivoting movement are performed by auxiliary electromechanical means, e.g., electric motor shafts or electrical linear drives or pneumatic lifting piston drives.

A medical supply unit is described in U.S. Pat. No. 3,431,937. It consists of two telescoping columns which are suspended on a ceiling, can be displaced one inside the other, and in which the pneumatic supply units needed for a medical device are led to a connection head, to which the working device is connected. A pivotable bracket acting as a receiving part is fastened to the connection head for the mechanical fastening of the working device. The connections for the media to be supplied, e.g., anesthesia gas and/or breathing gas for using an anesthesiological apparatus as a working device, are led from the supply ducts provided in the connection head to the device via appropriate supply lines.

The user must couple the working device, e.g., an anesthesiological apparatus, without further coupling aids, by fastening the anesthesiological apparatus to columns and bracket arms provided for this purpose by means of special screw connection means provided on the connection head. Correctly performed connecting and fastening can be checked only by checking the function of the connected working device. However, all connections are already firmly coupled, so that the entire device may have to be completely detached from the connection head in the case of incorrect coupling.

In an examination device according to DE-B-28,12,074, a working device in the form of a movable examination table is coupled to an X-ray apparatus, wherein the chassis is guided in rails, and the coupling devices engage in molded bodies provided for this purpose. If the chassis is correctly coupled with the examination table of the X-ray apparatus, a guide latch on the chassis engages in the switching contact of a switch fastened on the receiving head, thus signaling that the examination table can now be lowered onto the chassis.

In this prior-art examination device, only the correct position of the chassis relative to the height-adjustable connection head is ensured, but coupling of the examination table lowered onto the chassis standing by is not monitored, because the examination table can be lowered and be coupled into the coupling parts of the chassis only if the chassis is positioned in front of the height-adjustable column. It is not possible to check whether the frame of the examination table has been correctly coupled with the chassis. It may therefore happen that the incorrectly coupled examination table is transported unsecured on the chassis, without the user noticing it.

SUMMARY AND OBJECTS OF THE INVENTION

It is an object of the present invention to improve a supply unit of the above-described class such that the working device is coupled more reliably, so that the user will be able to perform a secured operation if the working device has been correctly coupled.

This task is accomplished in that the coupling part provided with guide slopes engages with a receiving part provided with receiving jaws extending in a complementary shape, and that vertically extending pins can be introduced into corresponding pin sockets provided on the working device in the case of a correctly fitting engagement.

The advantage of the present invention is essentially the fact that due to the working device being guided to the supply unit by means of the coupling part and the receiving part, correctly fitting positioning takes place. This then permits a pin-secured, reliable working holder to become engaged. Fastening of the working device on the supply unit and secured operation of the unit and of the working device, with the working device having been correctly coupled is thus possible.

The guide surfaces and receiving jaws on the coupling part and the receiving part, respectively, permit the working device, which is to be pushed toward the connection head in the horizontal direction, to be centered. To facilitate centering, the coordinated shaping of the guide surfaces and receiving jaws can be designed as angular introduction slopes, so that, e.g., a truncated cone-shaped coupling part will engage with a receiving part having a corresponding conical shape. A hemispherical coupling part and a cup-shaped receiving part can be considered to be another favorable combination. In the correctly coupled state, vertically extending pins on the receiving part will be able to extend into corresponding pin sockets provided on the working device on lowering the connection head.

If the supply unit and the working device are provided with a switching device, which is actuated in the coupled state, this switching device is able to cause the putting into operation of the working device and/or the connection head via electrical connections, such that the height adjustment of the connection head and/or the supply of the working device with the operating media will come into action.

It is achieved through this further method according to the present invention that the operation of the connection head and/or the working device depends on the correct coupling state, so that operation with working devices that have not been coupled at all or have been coupled incorrectly is impossible.

Operation of the working and supply devices is enabled only by actuation of the electrical contacts, e.g., REED contacts. The REED contacts make contact for the power supply to the control panel, which is indicated at the same time by a display lighting up, so that the operator knows that correct coupling has taken place and he can operate the control panel. Compressed gas or compressed oxygen, as well as electricity are usually provided as media necessary for operation both for the supply unit and its connection head and for the working device. These are channeled through the supply unit in appropriate ducts and led out at coupling openings provided on the connection head. Into these coupling openings the corresponding coupling plugs can be plugged either from the coupling part or from the working device.

If it is desirable to increase the reliability of a correctly coupled state, the coupling part should advantageously be provided with guide surfaces, and the receiving part should be provided with receiving jaws extending complementarily thereto, in addition to the switching device. The above-described advantages of the guide slopes and receiving jaws will be fully effective in this case as well.

The provision of pins on the receiving part, which extend into corresponding pin sockets in the coupled state, can be considered to represent a further improvement. Particularly secure and reliable coupling of the device with the supply unit is guaranteed in the case of this combined arrangement on the coupling part or the receiving part with a switching device for enabling the operation and with the pin holder.

To enable working devices with different heights to be connected to the connection head, it is advantageous to make the receiving part adjustable on vertically extending rails. Different working devices with greatly different overall heights are thus able to be received with their coupling part on a universal connection head.

It is also advantageous to provide the receiving part with a stop for controlling the position of the working device to be taken up. Structure for this stop can be designed pivotably by means of an adjusting device at least at right angles to the vertically extending connection plane between the working device and the receiving part. This offers the advantage that when coupling and suspending working devices of heavy weight, a vertically extending position of the coupled working device can be achieved despite the possible displacement of the vertical connection head from its vertical equilibrium position. In addition, it is thus possible to compensate for fit tolerances or manufacturing tolerances between the working device and the connection head. Since the adjusting device must be oriented pivotably in a vertical plane when coupling a working device with the vertically oriented connection head, it can additionally be favorable to design the adjusting device such that it can also be pivoted in the other two planes extending at right angles to the first plane, namely, in the plane separating the working device from the receiving part, on one hand, and in the plane in which the connection head is pivoted, on the other hand. Three-dimensional adjustability of the working device relative to the receiving part is thus achieved.

The space for installation of the control panel should be provided in an appropriate place at the operating height either on the working device or the receiving part. Thus, it is possible to monitor the working device and the connection head either on the basis of the control panel arranged on the working device, so that each working device will individually release, in the correctly coupled state, the working media specific for its operation; or the working media to be released are predetermined by the supply unit itself when the control panel is placed on the receiving part.

An ergonomically advantageous connection of the control panel in the immediate vicinity of a grip holder facilitates the operation of the working device or the receiving part in conjunction with the coupling of the working device with the supply unit.

If work is to be performed on the receiving part in connection with service or repair, it is necessary to operate the supply unit without the working device coupled to it. This is made possible by an insert, which can be inserted into the receiving jaws of the receiving part and which actuates the switching device. The insert may be designed, e.g., such that it consists of a spar that is provided with the guide faces which are inserted into the receiving jaws and will actuate the electrical contacts. Pin sockets, into which the pins provided on the receiving part will extend as soon as the insert is inserted, can also be provided on the insert.

In an advantageous variant, the insert is designed as a molded body, which is connected to the connection head and can be folded into the receiving jaws, wherein the electrical contacts, which release the connection head for putting into operation in the folded-in state, so that the control elements provided on the control panel for adjusting the height of the connection head will be active. If the supply unit is to be operated without a working device, it is no longer necessary to insert a loose insert into the receiving jaws, but the molded body is folded into the receiving jaws, and it will actuate the electrical contacts. The molded body is additionally provided with a projection, which serves as a support for the vertically positioning of the working device when the molded body has been folded back and the working device has been inserted.

If the electrical contacts on the receiving part are arranged in the vicinity of the pins, the projection can also be used to actuate the electrical contacts. If, for example, the electrical contacts are designed as REED contacts, the projection is equipped with a magnetic strip in the area of the REED contacts.

To facilitate the coupling and the connection of the media supplied from the supply unit into the working device coupled to it, it is advantageous to provide a supply block that can be connected to outlets of the supply canals on the face of the coupling part facing the receiving part. Either the supply block has plug-in contacts, which are introduced into the outlets of the supply ducts and connected when the working device has been coupled, or the supply block has connection lines with plug type couplers for the gaseous media needed for operation and plugs for the electricity, which can be plugged into corresponding sockets.

One embodiment of the present invention will be represented and described below in greater detail on the basis of a schematic drawing.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DETAILED DESCRIPTION OF THE PREFERRED EMBODIMENT

Figure 1:
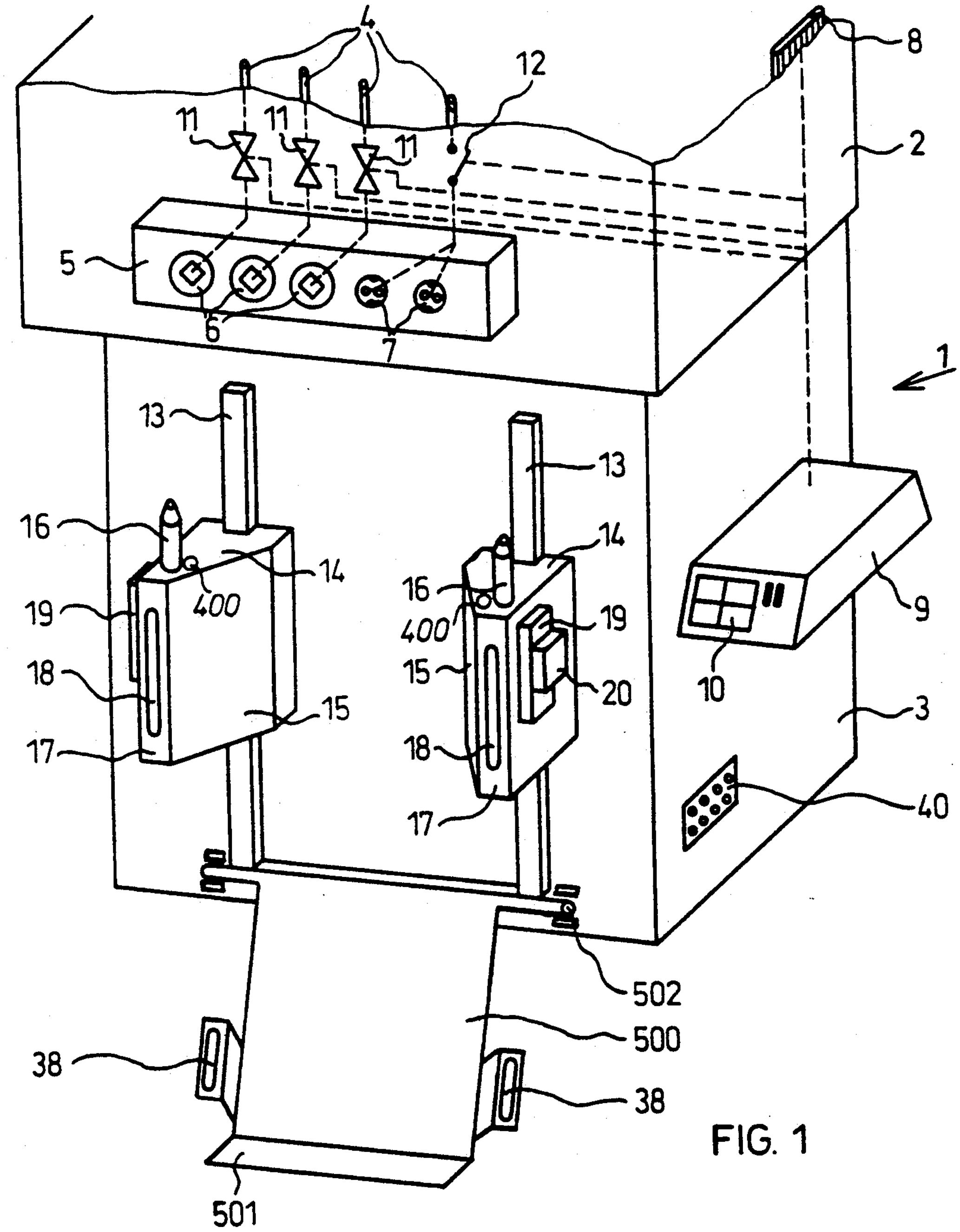
FIG. 1 is the partial perspective view of the connection head with the receiving part.
Figure 3:
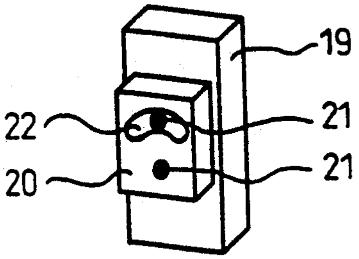
FIG. 3 is the side view of an adjustable stop for the coupling part.

The connection head 1 shown in FIG. 1 is composed of two parts (top part 2 and lower part 3) which are telescopingly displaceable one inside the other. The two parts 2, and 3 are adjustable in height one inside the other via a spindle drive (not shown). The supply ducts or canals 4, which consist of three compressed gas lines and one electric line, are located in the upper part 2. The supply canals 4 are led to a distributing connection means 5, which has appropriate plug type couplers 6 for the gas supply canals and sockets 7 for the electric power supply lines. The upper part 2 is extended up to the ceiling of a work room (not shown), and is mounted either rigidly or pivotably there. The supply canals 4 are also led to the ceiling within the upper part 2, and are directed from there to a gas supply unit (not shown) and a power supply unit (not shown), respectively. The motor drive (also not shown) for height adjustment, whose electrical control terminals are led via a flat strip cable 8 to a control panel 9, is also located inside the upper part 2. The control panel 9 is located outside the lower part 3 and has a control pad 10 for controlling the height adjustment. The control panel 9 is also connected electrically to the distributing connection 5, as a result of which a pneumatic valve 11 in one or several of the gas supply canals or an electric switch 12 in the power lines are actuated by depressing a corresponding switch of the control pad 10. The side of the lower part 3 facing the operator carries two vertically extending rails 13, on which one receiving part 14 each is displaceably fastened. The receiving parts 14 can be detached by means of a screw connection and displaced vertically along the rails, and fixed in the suitable height position. The receiving parts 14 have receiving jaws 15, which, facing one another, are designed such that together they enclose an acute angle pointing toward the operating surface of the lower part 3. A pin 16, which points in the vertical direction, is located on the top side of the receiving parts 14. Electrical contacts or switching means 18, which are designed as REED contacts in this embodiment, are recessed in the end faces 17 of the receiving parts 14. The electrical connections of the contacts are also led to the control panel 9, and their state of switching representing the state of coupling is indicated by a corresponding display in the control pad 10. A stop 19, which is shown in greater detail in FIG. 3, is located on the sides of the receiving parts 14 facing away from the receiving jaws 15. The stop 19 is a steel strip screwed onto the receiving part 14, on which an adjusting piece 20 is tiltably fastened by means of two square-head screws 21. After the screws 21 have been removed, the adjusting piece 20 can be adjusted in the zone of the kidney-shaped recess 22, and subsequently it can be blocked in this tilted position.

Figure 2:
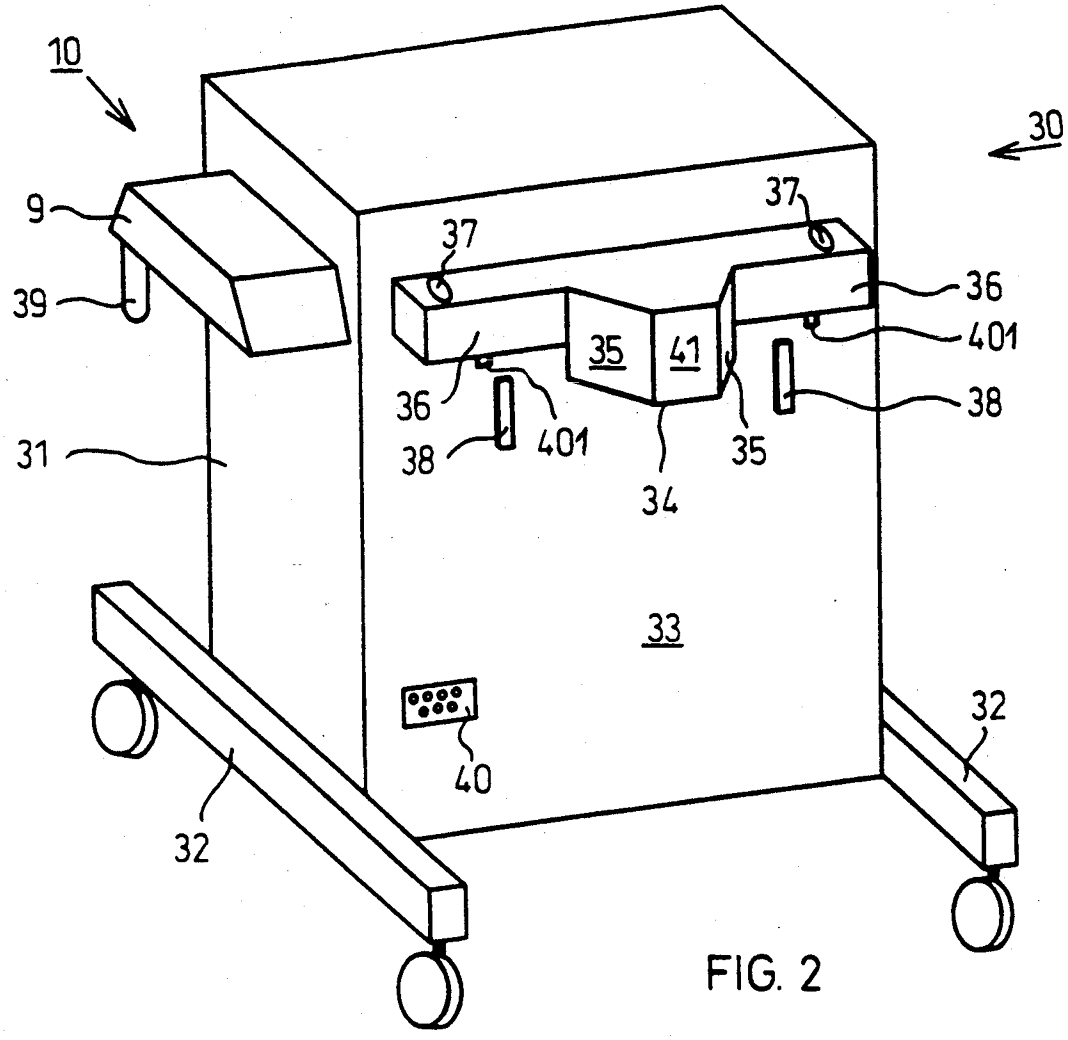
FIG. 2 is the rear perspective view of a working device with its coupling part.
Figure 4:
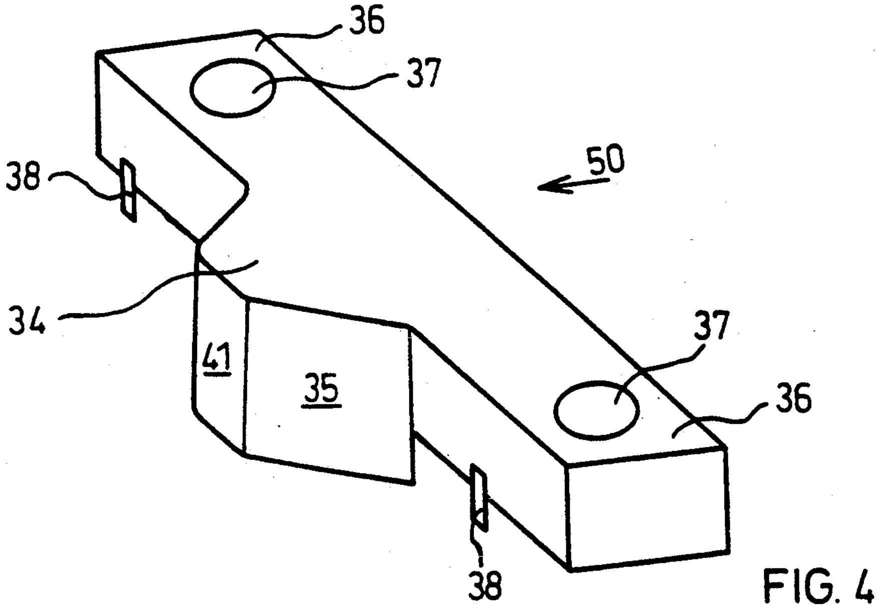
FIG. 4 is an insert for the receiving part.

FIG. 2 schematically shows a working device 30 as the housing 31 of an anesthesiological apparatus on a chassis 32, which has a coupling part 34 on its rear side 33. The shape of the coupling part 34 is adapted to the receiving part 14, i.e., it has—on its outer contour—guide faces 35 which are complementarily adapted to the receiving jaws 15. The guide faces 35 thus converge conically into a truncated end 41 of the coupling part 34. Two pin sockets 36, whose holes 37 fix the pins 16 when the working device 30 has been coupled, are located on the rear side 33 of the working device 30 at a laterally spaced location from the coupling part 34 and at the same height. Beneath the pin sockets 36, on the side of the guide faces 35, two contact pins 38, which are designed as magnetic strips actuating the REED contacts 18, are mounted on the rear side 33.

To couple the working device 30 to the connection head 1, its lower part 3 is first lowered by adjusting its height until the receiving parts 14 are positioned at the height of the coupling part 34. The working device 30 is then moved on its chassis 32 to the connection head 1, and its rear side 33 is pushed against the lower part 3 until the guide faces 35 of the coupling part 34 come into contact with the receiving jaws 15 of the receiving part 14. In the case of correct positioning and coupling, the holes 37 of the pin sockets 36 are located over the pins 16. At the same time, the magnetic strips 38 have actuated the REED contacts 18 and send a corresponding release signal to the control panel 9 optically displaying the release, so that the height adjustment of the connection head 1 can be performed by actuating the controls in the control pad 10 of the control panel 9. The lower part 3 will move upward, so that the pins 16 will be introduced into the holes 37 of the pin sockets 36, and the pin sockets 36 will rest on the receiving parts 14. Further rise of the lower part 3 will raise the working device 30 from its chassis 32, which can now be moved aside. Thus, the working device is suspended on the supply unit at a free distance above the floor of the room, on the ceiling of which the supply unit is suspended. Thus, the working device 30 is anchored in the pins 16 in the raised state, and is received by the receiving parts 14 in its position, so that the working device will reliably participate in horizontal pivoting movements. The vertical position of the entrained state is aligned vertically by the adjustable stops 19. In the case of correct coupling, the connection lines of the working device 30 can be connected to the distributing connection 5 of the upper part 2 of the supply unit, and the supply canals 4 can be connected to the working device 30 by actuating the valves 11 and the switches 12. To improve handling of the working device 30, which is coupled with and pivotably movable on the supply unit, the control panel 9 is provided with a grip 39. To send control signals from the working device 30 to the connection head 1, a multiple plug type control outlet 40 is arranged both on the rear side 33 of the working device 30 and on the sides of the lower part 3. Both plug type outlets may be connected to corresponding multiple cables.

As an alternative to data transmission via the multiple plug type outlet 40, a pair of first optocouplers 400, which are opposite a corresponding pair of second optocouplers 401 on the pin sockets 36, are arranged on the receiving parts 14 in the area of the pins 16. Each of the optocouplers 400, 401 is equipped with two transmission channels, so that a total of four transmission channels are available. The presence of four transmission channels also makes it possible to recognize the position when coupling the working device 30 to the connection head 1. Two channels, namely, one on the right side and the other on the left side of the optocouplers 400, 401, are used for signal transmission from the connection head 1 to the working device 30, and the other two channels are used to transmit a release signal from the working device 30 to the control panel 9. The control pad 10 can be operated only if the release signals of the right and left optocouplers 400 are received and displayed on the control panel 9.

To make it possible to operate the connection head 1 for maintenance or checking purposes even when the working device 30 is not coupled, an insert 50 is provided, which is equipped with the individual components necessary for the practical operation of the connection head 1. The insert 50 also has the pin sockets 36 with corresponding holes 37, and a coupling part 34 with corresponding guide faces 35, as well as a truncated end 41. The contact pins 38, designed as magnetic strips, for actuating the REED contacts 18 are arranged on the pin sockets 36 on the side of the guide faces 35. The insert 50 is placed with its pin sockets 36 onto the pins 16 of the receiving parts 14, as a result of which the receiving part 14 is blocked for coupling a working device 30, on one hand, and, on the other hand, the REED contacts 18 are actuated by the magnetic strips 38, and simulate the presence of a working device 30 for the supply unit, so that its function can be checked by means of the control panel 9. This checking pertains, e.g., to monitoring the height adjustment function, correct wiring arrangement of the valves 11 and correct wiring of the switches 12, in order to check the supply performance of the supply canals 4.

As an alternative to the insert 50, a molded body 500 can be provided, which can be folded into the receiving jaws 15, and in the folded-in state, the electrical contacts 18 are actuated via the contact pins 38, and the electrical contacts 18 release the connection head 1 for operation, such that the control elements 10 provided on the control panel 9 for adjusting the height of the connection head 1 are active. The molded body 500 is rotatable around an axis 502, and has a projection 501, can be in contact with the rear side 33 if the working device 30 is coupled, and acts as a support for the vertical positioning of the working device 30. In another variant, which is not shown here, the REED contacts 18 are arranged in the vicinity of the first optocouplers 400, and the projection 501 is designed as a contact pin. If the molded body 500 is folded into the receiving jaws 15, the contacts 18 are actuated by the projection 501, as a result of which the connection head 1 is released for being put into operation via the control panel 9.

What is claimed is:

1. A supply unit for supplying media to working devices, the supply unit comprising:
- a connection head moveable into a plurality of positions;
- a distributing connection means on said connection head for supplying the working device with the media;
- a coupling part mounted on the working device having guide faces;
- a receiving part mounted on said connection head, said receiving part having receiving jaws complimentary to said coupling part;
- one of said coupling part and said receiving part defining a bore; and
- a pin extending from the other of said coupling part and said receiving part, said pin engageable with said bore.

2. A supply unit in accordance with claim 1, further comprising:
- rail means for adjusting a position of said receiving part on said connection head.

3. A supply unit in accordance with claim 1, further comprising:
- stop means on said receiving part for controlling a position of the working device.

4. A supply unit in accordance with claim 3, wherein:
- said stop means has an adjusting device pivotable at least a right angles to the plane connecting said receiving part and the working device.

5. A supply unit in accordance with claim 1, further comprising:
- optocouplers mounted on said receiving part and said coupling part, for transferring information between the working device and said connection head.

6. A supply unit in accordance with claim 5, wherein:
- said transferred information includes degree of engagement of said coupling part and said receiving part.

7. A supply unit for supplying media to working devices, the supply unit comprising:
- a connection head moveable into a plurality of positions;
- a distributing connection means on said connection head for supplying the working device with the media;
- a coupling part mounted on the working device;
- a receiving part mounted on said connection head said receiving part engaging said coupling part;
- switching means on said connection head and the working device for generating a coupling signal representing the state of coupling of said connection head and the working device; and
- a control panel for receiving said coupling signal and for controlling movement of said connection head and said supply of the media.

8. A supply unit in accordance with claim 7, further comprising:
- receiving jaws on said receiving part complimentary to said coupling part for receiving and engaging said coupling part.

9. A supply arrangement according to claim 7, wherein said coupling part is equipped with guide faces and said receiving part is provided with complementary extending receiving jaws, said guide faces being engagable with said complementary extending receiving jaws.

10. A supply unit in accordance with claim 7, further comprising:
- one of said coupling part and said receiving part defining a bore; and
- a pin extending from the other of said coupling part and said receiving part and said pin engagable with said bore.

11. A supply unit in accordance with claim 7, wherein:
- said control panel is arranged at an operating height on the working device.

12. A syupply unit in accordance with claim 7, wherein:
- said control panel is arranged at an operating height on said connection head.

13. A supply unit in accordance with claim 7, further comprising:

a grip holder arranged in proximity to said control panel.

14. A supply unit in accordance with claim 7, further comprising:

an insert means for engaging with said receiving part and actuating said switching means to generate said coupling signal, said control panel only controlling said movement of said connection head and said supply of the media when receiving said coupling signal.

15. A supply unit in accordance with claim 7, further comprising:

a molded body mounted on said connection head and pivotable into a first position engaging said receiving part, said molded body in said first position actuating said switching means to generate said coupling signal.

16. A supply unit in accordance with claim 15, wherein:

said molded body has a projection and is pivotable into a second position for positioning and supporting the working device when the working device is engaged to said connection head.

17. A supply unit in accordance with claim 16, wherein:

said projection of said molded body actuates said switching means when said molded body is in said first position.

18. A supply unit for supporting a working device and supplying the working device with media, the supply unit comprising:

a connection head mountable on a ceiling and movable into a plurality of positions, said connection head containing a supply duct for transferring the media to the working device;

a distributing connection means on said connection head for connecting said supply duct to the working device;

a receiving part mounted on said connection head having guide faces;

a coupling part mounted on the working device, said coupling device shaped complimentary to said receiving part for engagement with said receiving part said engagement being guided by said guide faces of said receiving part;

one of said coupling part and said receiving part defining a bore;

a pin extending from the other of said coupling part and said receiving part, said pin engagable with said bore when said coupling part is engaged with said receiving part;

switching means on said connection head and the working device for generating a coupling signal representing the state of coupling of said connection head and the working device;

a control panel for receiving said coupling signal and for controlling movement of said connection head and said supply of the media, said control panel controlling upward movement of said connection head after said coupling signal is received, said upward movement engaging said pin with said bore, and said engagement of said pin with said bore, with said engagement of said coupling part with said receiving part, forming support of the working device during lifting of the working device by said upward movement of said connection head.

19. A supply unit in accordance with claim 18, wherein:

said upward movement of said connecting head connects said distribution connection with the working device.

20. A supply unit in accordance with claim 18, further comprising:

control outlets on said connection head and the working device for transmitting information between said connection head and the working device.

* * * * *